(12) United States Patent
Garrett

(10) Patent No.: US 7,288,535 B2
(45) Date of Patent: Oct. 30, 2007

(54) METHODS AND COMPOSITIONS FOR STIMULATING BONE GROWTH USING NITRIC OXIDE RELEASING BISPHOSPHONATE CONJUGATES

(75) Inventor: I. Ross Garrett, San Antonio, TX (US)

(73) Assignee: OsteoScreen, Inc., San Antonio, TX (US)

( * ) Notice: Subject to any disclaimer, the term of this patent is extended or adjusted under 35 U.S.C. 154(b) by 185 days.

(21) Appl. No.: 10/428,309

(22) Filed: May 2, 2003

(65) Prior Publication Data

US 2004/0014727 A1 Jan. 22, 2004

Related U.S. Application Data

(60) Provisional application No. 60/377,898, filed on May 2, 2002.

(51) Int. Cl.
*A61K 31/66* (2006.01)
*A61K 31/445* (2006.01)

(52) U.S. Cl. ............... 514/102; 514/108; 514/327

(58) Field of Classification Search ........ 514/632, 514/742
See application file for complete search history.

(56) References Cited

U.S. PATENT DOCUMENTS

| 5,280,040 | A | | 1/1994 | Labroo et al. ............ 514/422 |
|---|---|---|---|---|
| 5,442,102 | A | | 8/1995 | Tognella et al. |
| 5,898,038 | A | * | 4/1999 | Yallampalli et al. ........ 514/742 |
| 6,121,253 | A | * | 9/2000 | Han et al. .................. 514/102 |
| 6,133,320 | A | | 10/2000 | Yallampalli et al. |
| 6,214,812 | B1 | * | 4/2001 | Karpeisky et al. ............ 514/89 |
| 6,573,252 | B1 | | 6/2003 | Del Soldato ............... 514/108 |

FOREIGN PATENT DOCUMENTS

| EP | 0 514 720 | 11/1992 |
|---|---|---|
| WO | WO-00/06585 | 2/2000 |
| WO | WO-00/51597 | 9/2000 |
| WO | WO-00/61537 | 10/2000 |
| WO | WO-01/12584 | 2/2001 |

OTHER PUBLICATIONS

Wallace, Dicay, Mcknight, Bastaki and Blank; N-bisphosphonates cause gastric epithelial injury independent of effects on the microcirculation: Alimentary Pharmacology & Therapeutics; vol. 13 Issue 12 p. 1675 www.blackwell-synergy.com, retrieved May 3, 2005.*
S. J. Wimalawansa, G. De Marco, P. Gangula and C. Yallampalli: Nitric oxide donor alleviates ovariectomy-induced bone loss; Bone vol. 18, Issue 4, Apr. 1996, pp. 301-304.*
Fiorucci et al. Nitric Oxide-Releasing NSAIDs Drug safety : an international journal of medical toxicology and drug experience, (2001) 24 (11) 801-11.*
Bellows, C.G. et al., Develop Biol 140:132-38 (1990).
Ducy, P. et al., Nature 382:448-52 (1996).
Harris, S. et al., "Expression of bone morphogenetic protein messenger RNA in prolonged cultures of fetal rat calvarial cells" J Bone Miner Res. 9(3):389-94 (1994).
Rickard, D.J. et al., Develop Biol 161:218-28 (1994).
Supplementary Partial European Search Report for EP 03724391.2, mailed on Feb. 21, 2006, 7 pages.

* cited by examiner

*Primary Examiner*—Raymond J. Henley, III
(74) *Attorney, Agent, or Firm*—Morrison & Foerster LLP

(57) ABSTRACT

The invention relates to compositions and methods for use in treating skeletal system disorders in a vertebrate at risk for bone loss, and in treating conditions that are characterized by the need for bone growth, in treating fractures, and in treating cartilage disorders. More specifically, the invention concerns the use of NO-bisphosphonate assembly for enhancing bone growth.

10 Claims, No Drawings

METHODS AND COMPOSITIONS FOR STIMULATING BONE GROWTH USING NITRIC OXIDE RELEASING BISPHOSPHONATE CONJUGATES

CROSS-REFERENCE TO RELATED APPLICATIONS

This Application claims priority under 35 U.S.C. § 119(e) to U.S. Ser. No. 60/377,898 filed 2 May 2002.

TECHNICAL FIELD

The invention relates to compositions and methods for use in treating skeletal system disorders in a vertebrate at risk for bone loss, and in treating conditions that are characterized by the need for bone growth, in treating fractures, and in treating cartilage disorders. More specifically, the invention concerns the use of NO-bisphosphonate activity, e.g., a NO-bisphosphonate compound, for enhancing bone growth.

BACKGROUND OF THE INVENTION

Bone is subject to constant breakdown and re-synthesis in a complex process mediated by osteoblasts, which produce new bone, and osteoclasts, which destroy bone. The activities of these cells are regulated by a large number of cytokines and growth factors, many of which have now been identified and cloned.

There is a plethora of conditions which are characterized by the need to enhance bone formation or to inhibit bone resorption. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.

Bone fractures are still treated exclusively using casts, braces, anchoring devices and other strictly mechanical means. Further bone deterioration associated with post-menopausal osteoporosis has been treated with estrogens or bisphosphonates, which may have drawbacks for some individuals. Treatment of bone or other skeletal disorders, such as those associated with cartilage, can be achieved either by enhancing bone formation or inhibiting bone resorption or both.

Bone tissue is an excellent source for factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these latter factors are transforming growth factor β, the heparin-binding growth factors (e.g., acidic and basic fibroblast growth factor), the insulin-like growth factors (e.g., insulin-like growth factor I and insulin-like growth factor II), and a recently described family of proteins called bone morphogenetic proteins (BMPs). All of these growth factors have effects on other types of cells, as well as on bone cells.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase. They also synthesize a number of growth regulatory peptides which are stored in the bone matrix, and are presumably responsible for normal bone formation. These growth regulatory peptides include the BMPs (Harris S., et al. (1994), supra). In studies of primary cultures of fetal rat calvarial osteoblasts, BMPs 1, 2, 3, 4, and 6 are expressed by cultured cells prior to the formation of mineralized bone nodules (Harris S., et al. (1994), supra). Like alkaline phosphatase, osteocalcin and osteopontin, the BMPs are expressed by cultured osteoblasts as they proliferate and differentiate.

These data are, however, contrary to reports that dexamethasone and other inducers, such as BMPs, induce osteoblastic differentiation and stimulate osteocalcin mRNA (Bellows, C. G., et al., *Develop Biol* (1990) 140:132-38; Rickard, D. J., et al., *Develop Biol* (1994) 161:218-28). In addition, Ducy, P., et al., *Nature* (1996) 382:448-52 have recently reported that osteocalcin deficient mice exhibit a phenotype marked by increased bone formation and bones of improved functional quality, without impairment of bone resorption. Ducy, et al., state that their data suggest that osteocalcin antagonists may be of therapeutic use in conjunction with estrogen replacement therapy (for prevention or treatment of osteoporosis). However, there continues to be a need for additional treatments to stimulate bone growth or to mitigate bone loss.

Bisphosphonates, formerly called diphosphonates are compounds characterized by two C—P bonds. If the two bonds are located on the same carbon atom, resulting in a P—C—P structure, the compounds are called germinal bisphosphonates. They are therefore analogues of pyrophosphate that contain a carbon instead of an oxygen. There are a number of known pharmacologically active bisphosphonates including alendronate, Clodronate, etidronate, ibandronate, icadronate, pamidronate, risedronate, tiludronate and zoledronate. The main effect of these pharmacologically active bisphosphonates is to inhibit resorption both in vitro and in vivo. These effects are related to the marked affinity of these compounds for solid-phase calcium phosphate, on the surface of bone to which they bone strongly. In essence they target bone and elicit there pharmacological inhibition of osteoclast activity there. The mode of action of the bisphosphonates is still not completely elucidated. There is no doubt that their action in vivo is mediated mostly, if not completely, through mechanisms other than the physicochemical inhibition of crystal dissolution. There is a general consensus that the bisphosphonates act by inhibiting the activity of osteoclasts. Osteoclasts are inhibited when they come into contact with bisphosphonates-containing bone. This supports the hypothesis that bisphosphonates are deposited onto bone because of their strong affinity for the mineral, and that the osteoclasts are then inhibited when they start to engulf bisphosphonates-containing bone. The biochemical mechanisms by which bisphosphonates inhibit osteoclast activity are still unclear and may well be that more than one mechanism is operating.

The bisphosphonates investigated up to now appear to be absorbed, stored, and excreted unaltered in the body. Thus, bisphosphonates seem to be non-biodegradable, both in animals and in solution. Most of the pharmacokinetics data on the bisphosphonates have been obtained with etidronate, clodronate and pamidronate. The intestinal absorption lies between 1% and 10%. Between 20% and 50% of the absorbed bisphosphonate is localized to the bone, the remainder being rapidly excreted in the urine.

Although the nitrogen-containing bisphosphonates such as alendronate and pamidronate, have been shown to be effective in preventing the bone loss these drugs also appear capable of causing injury to the upper gastrointestinal tract and their have been several case reports of severe oesophagitis in patients treated with alendronate. Alendronate has also been shown to cause erosions and ulcers in the human stomach and to interfere with the healing of pre-existing lesions when given to healthy volunteers at doses that are prescribed for the treatment of osteoporosis and Pagets disease of bone.

The half-life of circulating bisphosphonates is short, in the rat only of the order of minutes. In man it is somewhat longer, about 2 hours. Acute, subacute, and chronic administration in several animal species have revealed little toxicity. Teratogenic, mitogenic and carcinogenic tests have been negative.

Other agents appear to operate by preventing the resorption of bone. Thus, U.S. Pat. No. 5,280,040 discloses compounds described as useful in the treatment of osteoporosis. These compounds putatively achieve this result by preventing bone resorption.

Nitric oxide (NO) has recently been shown to have profound effects on the metabolic activity of bone. This biologically active molecule generated biologically by a set of enzymes called nitric oxide synthases. Three known forms of the enzyme exist. Firstly, iNOS which is the inducible form where the expression of the enzyme and therefore the production of nitric oxide can be induced by a number of inflammatory stimuli. Secondly eNOS which is the constitutive form which is cannot be induced.

Endothelial dysfunction defined as the impaired ability of vascular endothelium to stimulate vasodilation plays a key role in the development of atherosclerosis and in various pathological conditions which predispose to atherosclerosis, such as hypercholesterolemia, hypertension, type 2 diabetes, hyperhomocyst (e) inemia and chronic renal failure. The major cause of the endothelial dysfunction is decreased bioavailability of nitric oxide (NO), a potent biological vasodilator produced in vascular endothelium from L-arginine by the endothelial NO synthase (eNOS). In vascular diseases, the bioavailability of NO can be impaired by various mechanisms, including decreased NO production by eNOS, and/or enhanced NO breakdown due to increased oxidative stress. The deactivation of eNOS is often associated with elevated plasma levels of its endogenous inhibitor, N(G) N(G)-dimethyl-L-arginine (ADMA). In hypercholesterolemia, a systemic deficit of NO may also increase the levels of low density lipoproteins (LDL) by modulating its synthesis and metabolism by the liver, as suggested by recent in vivo and in vitro studies using organic NO donors. Therapeutic strategies aiming to reduce the risk of vascular diseases by increasing bioavailability of NO continue to be developed.

Nitric oxide (NO) is a free radical which has important effects on bone cell function. The endothelial isoform of nitric oxide synthase (eNOS) is widely expressed in bone on a constitutive basis, whereas inducible NOS is only expressed in response to inflammatory stimuli. It is currently unclear whether neuronal NOS is expressed by bone cells. Pro-inflammatory cytokines such as IL-1 and TNF cause activation of the iNOS pathway in bone cells and NO derived from this pathway potentiates cytokine and inflammation induced bone loss. These actions of NO are relevant to the pathogenesis of osteoporosis in inflammatory diseases such as rheumatoid arthritis, which are characterized by increased NO production and cytokine activation. Interferon gamma is a particularly potent stimulator of NO production when combined with other cytokines, causing very high concentrations of NO to be produced. These high levels of NO inhibit bone resorption and formation and may act to suppress bone turnover in severe inflammation. The eNOS isoform seems to play a key role in regulating osteoblast activity and bone formation since eNOS knockout mice have osteoporosis due to defective bone formation. Other studies have indicated that the NO derived from the eNOS pathway acts as a mediator of the effects of estrogen in bone. eNOS also mediates the effects of mechanical loading on the skeleton where it acts along with prostaglandins, to promote bone formation and suppress bone resorption. Pharmacological NO donors have been shown to increase bone mass in experimental animals and preliminary evidence suggests that these agents may also influence bone turnover in man. These data indicate that the L-arginine/NO pathway represents a novel target for therapeutic intervention in the prevention and treatment of bone diseases.

Because of the importance of nitric oxide in many biological events numerous NO releasing compounds are now being synthesized. Many of these involve the use of linking NO to non-steroidal anti-inflammatory drugs (NSAIDS) such as flurbiprofen, ketoprofen, diclofenac and naproxen. These agent have been shown to spare the GI-tract from the undesired effects the NSAIDs by increasing blood flow and mucus secretion as well as reducing free radical generation in the stomach.

SUMMARY OF THE INVENTION

In one aspect, the present invention is directed to a method to enhance bone formation or bone mineral density, or to treat a pathological bone condition or to treat a degenerative joint condition in a vertebrate subject, which method comprises administering to a vertebrate subject in need of such treatment an effective amount of a bisphosphonate to which is attached nitric oxide in a form which can be released (NO-bisphosphonate), whereby bone formation or bone mineral density is enhanced, or said pathological bone condition or degenerative joint condition is treated, in said vertebrate subject. The NO-bisphosphonate can be used alone, in combinations, or can be used in conjunction with an additional or secondary agent that promotes bone growth or inhibits bone resorption.

In another aspect, the present invention is directed to a combination, preferably in the form a pharmaceutical composition, which combination comprises a NO-bisphosphonate compound and a non NO-bisphosphonate compound that promotes bone growth or inhibits bone resorption. Kits and articles of manufactures comprising a NO-bisphosphonate compound, whether alone, in combinations, or with a non-NO-bisphosphonate compound that promotes bone growth or inhibits bone resorption, also are provided.

Any suitable bone enhancer or bone resorption inhibitor can be used in the combination. Exemplary of such agents that can be used in the combination include bone morphogenetic factors, anti-resorptive agents, osteogenic factors, cartilage-derived morphogenetic proteins, growth hormones, estrogens, bisphosphonates, statin, differentiating factors, compounds that inhibit activity of NF-κB, e.g., anti-NF-κB antibodies, compounds that inhibit production of NF-κB, e.g., anti-NF-κB antisense oligos, compounds that inhibit activity of proteasomal activity, e.g., antibodies that specifically bind to proteasomal proteins, and compounds that inhibits production of a proteasome protein, e.g., antisense oligos that are complementary to genes or RNAs that encode proteasomal proteins. For clinical uses, the antibodies are preferably monoclonal or humanized antibodies.

DETAILED DESCRIPTION OF THE INVENTION

In accordance with the present invention, there are provided methods of treating bone defects (including osteoporosis, fractures, osteolytic lesions and bone segmental defects) in subjects suffering therefrom said method comprising administering to said subject, in an amount sufficient to stimulate bone growth, a NO-bisphosphonate.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails.

As used herein, "a" or "an" means "at least one" or "one or more." As used herein, "or" means in the alternative as well as in combination.

As used herein, "enhance" means to promote, increase, or stimulate bone formation or growth, or bone mineral density, in a vertebrate animal.

As used herein, "an effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms. Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art.

As used herein, "pharmaceutically acceptable salts, esters or other derivatives" include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, "treatment" means any manner in which the symptoms of a conditions, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether pennanent or temporary, lasting or transient that can be attributed to or associated with administration of the composition.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "antibody" includes antibody fragments, such as Fab fragments, which are composed of a light chain and the variable region of a heavy chain.

As used herein, "humanized antibodies" refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

The term "substantially" identical or homologous or similar varies with the context as understood by those skilled in the relevant art and generally means at least 70%, preferably means at least 80%, more preferably at least 90%, and most preferably at least 95% identity.

As used herein, a "composition" refers to any mixture. It may be a solution, a suspension, liquid, powder, paste, aqueous, non-aqueous or any combination thereof.

As used herein, a "combination" refers to any association between two or among more items.

As employed herein, the term "subject" embraces human as well as other animal vertebrate species, such as, for example, canine, feline, bovine, porcine, rodent, and the like. It will be understood by the skilled practitioner that the subject is one appropriate to the desirability of enhancing bone formation or bone mineral density. Preferably the subject is a mammal, more preferably a primate, and most preferably a human.

As used herein, "treat" or "treatment," as related to bone growth defects, include a postponement of development of bone deficit symptoms and/or a reduction in the severity of such symptoms that will or are expected to develop. These terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired. "Bone disorders" includes both bone deficits and cartilage defects.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. Methods for Enhancing Bone Formation and Uses Thereof

In one aspect, the present invention is directed to a method to enhance bone formation or bone mineral density, or to treat a pathological bone condition or to treat a degenerative joint condition in a vertebrate subject, which method comprises administering to a vertebrate subject in need of such treatment an effective amount of a NO-bisphosphonate, whereby bone formation or bone mineral density is enhanced, or said pathological bone condition or degenerative joint condition is treated, in said vertebrate subject. The compound can be used alone or can be used in conjunction with an additional or secondary agent that promotes bone growth or inhibits bone resorption.

Any NO-bisphosphonate can be used in the present method. In particular this includes specific NO-bisphosphonate such as NO-(4-animo-1-hydroxybutylidene)bis-phosphonate (NO-alendronate), NO-(3-Amino-1-hyroxypropylidene)bis-phosphonate (NO-pamidronate), NO-(Dichlorormethylene)-bis-phosphonate, (NO-clodronate), NO-[1-Hydroxy-2(3-pyridinyl)-ethylidene]-bis-phosphonate (NO-risedronate), NO-[1-Hyroxy-2-(1H-imidazole-1-yl)ethylidene]-bis-phosphonate (NO-zolondronate), NO-(1-Hydroxyethylidene)-bis-phosphonate (NO-etidronate), NO-[1-Hydroxy-3-(methylpentylamino)propylidene]-bis-phosphonate (NO-ibandronate), NO-[[(4-Clorophenyl)thio]methylene]-bis-phosphonate (NO-tiludronate), NO-(6-Amino-1-hydroxyhexylidene)-bis-phosphonate (NO-neridronate), NO-([3-(Dimethylamino)-1-hydroxypropylidene]-bis-phosphonate (NO-olpadronate), NO-[(Cycloheptylamino)-methylene]-bis-phosphonate (NO-icadronate) and NO-[1-Hydroxy-2-imidazo-(1,2-a)pyridine-3-ylethylidene]-bis-phosphonate (NO—YH529).

The present method can be used for treating any diseases, disorders or conditions that are associated with bone formation defects, whether caused by defective bone growth, over-active bone resorption or both. Any pathological dental conditions or degenerative joint conditions can be treated with the present method. Exemplary conditions that can be treated by the present method include osteoporosis, bone fracture or deficiency, bone segmental defects, primary or secondary hyperparathyroidism, periodontal disease or defect, metastatic bone disease, osteolytic bone disease, post-plastic surgery, post-prosthetic joint surgery, and post-dental implantation.

Other uses of the present method include, but are not limited to, repair of bone defects and deficiencies, such as those occurring in closed, open and non-union fractures; prophylactic use in closed and open fracture reduction; promotion of bone healing in plastic surgery; stimulation of bone in-growth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, diabetes-related osteoporosis, glucocorticoid-induced or related osteoporosis, or disuse osteoporosis and arthritis, or any condition that benefits from stimulation of bone formation; repair of congenital, trauma-induced or surgical resection of bone (for instance, for cancer treatment) and in cosmetic surgery; limiting or treating cartilage defects, injuries or disorders; and may be useful in wound healing or tissue repair.

C. Combinations, Kits and Articles of Manufacture

In a specific embodiment, the present method can further comprise administering to the subject an additional agent that promotes bone growth or inhibits bone resorption. The NO-bisphosphonate and the secondary agent can be administered simultaneously or sequentially.

Any suitable bone enhancer or bone resorption inhibitor can be used in this combination therapy as the additional agent. Exemplary compounds that can be used in the combination therapy include bone morphogenetic factors, anti-resorptive agents, osteogenic factors, cartilage-derived morphogenetic proteins, growth hormones, estrogens, bisphosphonates, statin, differentiating factors, compounds that inhibit activity of NF-κB, compounds that inhibit production of NF-κB, compounds that inhibit activity of proteasomal activity and compounds that inhibits production of a proteasome protein. Preferably, these compounds used for enhancing bone formation or treating pathological dental conditions or degenerative joint conditions are disclosed below and those that are disclosed in the following published PCT International Patent Applications also can be used: PCT/US 00/41360, filed Oct. 20, 2000; and WO 00/02548.

Small molecules which are able to stimulate bone formation have been disclosed in PCT applications WO98/17267 published 30 Apr. 1998, WO97/15308 published 1 May 1997 and WO97/48694 published 24 Dec. 1997. These agents generally comprise two aromatic systems spatially separated by a linker. In addition, PCT application WO98/25460 published 18 Jun. 1998, discloses the use of the class of compounds known as statins in enhancing bone formation.

The NO-bisphosphonate and additional agent can be formulated in a single pharmaceutical composition. Alternatively, they can be formulated as separate pharmaceutical compositions.

Other known inhibitors of proteasomal activity, NF-κB or both can be ascertained from the literature or compounds can be tested for these activities using assays known in the art. In addition, inhibitors, e.g., antisense polynucleotides, which lower the level of effective expression of the nucleotide sequence encoding the enzymes that have proteasomal activity or of the nucleotide sequence encoding NF-κB can be assessed and used in the invention methods. Also provided are compounds such as sulfasalazine, sulfasalazine (Liptay, et al., *Br. J. Pharmacol.*, 128(7):1361-9 (1999)); and Wahl, et al., *J. Clin. Invest.*, 101(5):1163-74 (1998)) and calpain inhibitor II.

E. Assays for NO-bisphosphonate

Numerous assays can be used to identify and/or assess the efficacy of compounds that can be used in the present methods and combinations or pharmaceutical compositions.

The production of nitric oxide in cell culture media, serum or plasma can be measured by using available assay kits for total nitric oxide (R&D systems) as well as Nitrite/Nitrate ($NO_2^-/NO_3^-$) kits (R&D systems). Intracelluar activation of soluble guanylate cyclase by nitric oxide can be measured by the use of cyclic AMP/GMP enzyme immunoassay kits (Cayman, Ann Arbor).

Screening Assays—Bone

The osteogenic activity of the compounds used in the methods of the invention can be verified using in vitro screening techniques, such as the assessment of transcription of a reporter gene coupled to a bone morphogenetic protein-associated promoter or in alternative assays.

Techniques for ABA Screening Assay

A rapid throughput screening test for compounds that stimulate bone formation by demonstration that they are capable of stimulating expression of a reporter gene linked to a BMP promoter (a surrogate for the production of bone morphogenetic factors that are endogenously produced) is described in U.S. application Ser. No. 08/458,434, filed 2 Jun. 1995, the entire contents of which are incorporated herein by reference. This assay is also described as a portion of a study of immortalized murine osteoblasts (derived from a mouse expressing a transgene composed of a BMP2 promoter driving expression of T-antigen) in Ghosh-Choudhery, N., et al., *Endocrinology* (1996) 137:331-39. In this study, the immortalized cells were stably transfected with a plasmid containing a luciferase reporter gene driven by a mouse BMP2 promoter (−2736/114 bp), and responded in a dose-dependent manner to recombinant human BMP2.

Briefly, the assay utilizes cells transformed permanently or transiently with constructs in which the promoter of a bone morphogenetic protein, specifically BMP2 or BMP4, is coupled to a reporter gene, typically luciferase. These transformed cells are then evaluated for the production of the reporter gene product; compounds that activate the BMP promoter will drive production of the reporter protein, which can be readily assayed. Many thousands of compounds have been subjected to this rapid screening technique, and only a very small percentage are able to elicit a level of expression of reporter gene 5-fold greater than that produced by vehicle. Compounds that activate the BMP promoter fall into groups, where members of each group share certain structural characteristics not present in inactive compounds. The active compounds ("BMP promoter-active compounds" or "active compounds") are useful in promoting bone or cartilage growth, and thus in the treatment of vertebrates in need of bone or cartilage growth.

BMP promoter-active compounds can be examined in a variety of other assays that test specificity and toxicity. For instance, non-BMP promoters or response elements can be linked to a reporter gene and inserted into an appropriate host cell. Cytotoxicity can be determined by visual or microscopic examination of BMP promoter- and/or non-BMP promoter-reporter gene-containing cells, for instance. Alternatively, nucleic acid and/or protein synthesis by the cells can be monitored. For in vivo assays, tissues may be removed and examined visually or microscopically, and optionally examined in conjunction with dyes or stains that facilitate histologic examination. In assessing in vivo assay results, it may also be useful to examine biodistribution of the test compound, using conventional medicinal chemistry/animal model techniques.

Techniques for Neonatal Mouse Calvaria Assay (In Vitro)

An assay for bone resorption or bone formation is similar to that described by Gowen M. & Mundy G., *J Immunol* (1986) 136:2478-82. Briefly, four days after birth, the front and parietal bones of ICR Swiss white mouse pups are removed by microdissection and split along the sagittal suture. In an assay for resorption, the bones are incubated in BGJb medium (Irvine Scientific, Santa Ana, Calif.) plus 0.02% (or lower concentration) β-methyleyclodextrin, wherein the medium also contains test or control substances. The medium used when the assay is conducted to assess bone formation is Fitton and Jackson Modified BGJ Medium (Sigma) supplemented with 6 ug/ml insulin, 6 ug/ml transferrin, 6 ng/ml selenous acid, calcium and phosphate concentrations of 1.25 and 3.0 mM, respectively, and ascorbic acid to a concentration of 100 ug/ml is added every two days. The incubation is conducted at 37° C. in a humidified atmosphere of 5% $CO_2$ and 95% air for 96 hours.

These neonatal murine calvaria do contain measurable levels of alkaline phosphatase and this can be measured either from the calvaria itself or to some degree in the incubation media as a semi-quantitative measurement of bone formation activity. For measurement of alkaline phosphatase activity in the media, 50 ul is removed at the end of the assay. The activity is then measured using standard alkaline phosphatase reagents.

The bones are removed from the incubation media and fixed in 10% buffered formalin for 24-48 hours, decalcified in 14% EDTA for 1 week, processed through graded alcohols; and embedded in paraffin wax. Three μm sections of the calvaria are prepared. Representative sections are selected for histomorphometric assessment of bone formation or bone resorption. Bone changes are measured on sections cut 200 μm apart. Osteoblasts and osteoclasts are identified by their distinctive morphology.

Other auxiliary assays can be used as controls to determine non-BMP promoter-mediated effects of test compounds. For example, mitogenic activity can be measured using screening assays featuring a serum-response element (SRE) as a promoter and a luciferase reporter gene. More specifically, these screening assays can detect signaling through SRE-mediated pathways, such as the protein kinase C pathway. For instance, an osteoblast activator SRE-luciferase screen and an insulin mimetic SRE-luciferase screen are useful for this purpose. Similarly, test compound stimulation of cAMP response element (CRE)-mediated pathways can also be assayed. For instance, cells transfected with receptors for PTH and calcitonin (two bone-active agents) can be used in CRE-luciferase screens to detect elevated cAMP levels. Thus, the BMP promoter specificity of a test compound can be examined through use of these types of auxiliary assays.

F. Formulations and Administrations

The NO-bisphosphonate, whether alone or in combination with an additional agent that promotes bone, may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, latest edition, Mack Publishing Co., Easton Pa., which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in PCT publication WO 93/20859, which is incorporated herein by reference. Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins (U.S. Pat. No. 4,761,471; PCT Publication WO90/11366), osteogenin (Sampath, et al., *Proc. Natl. Acad. Sci. USA* (1987) 84:7109-13) and NaF (Tencer, et al., *J. Biomed. Mat. Res.* (1989) 23: 571-89) are also preferred. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds of the present invention include use of ALZET™ osmotic minipumps (Alza Corp., Palo Alto, Calif.); sustained release matrix materials such as those disclosed in Wang, et al. (PCT Publication WO 90/11366); electrically charged dextran beads, as disclosed in Bao, et al. (PCT Publication WO 92/03125); collagen-based delivery systems, for example, as disclosed in Ksander, et al., *Ann. Surg.* (1990) 211(3):288-94; methylcellulose gel systems, as disclosed in Beck, et al., *J. Bone Min. Res.* (1991) 6(11):1257-65; alginate-based systems, as disclosed in Edelman, et al., *Biomaterials* (1991) 12:619-26 and the like. Other methods well known in the art for sustained local delivery in bone include porous coated metal prostheses that can be impregnated and solid plastic rods with therapeutic compositions incorporated within them.

The compounds of the present invention may also be used in conjunction with agents that inhibit bone resorption. Antiresorptive agents, such as estrogen, bisphosphonates and calcitonin, are preferred for this purpose. More specifically, the compounds disclosed herein may be administered for a period of time (for instance, months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be administered with an anti-resorptive compound in a cyclical manner (administration of disclosed compound, followed by anti-resorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, as well as other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D., et al., *J Mol Biol* (1965) 23:238-252, Olson, F., et al., *Biochim Biophys Acta* (1979) 557:9-23, Szoka, F., et al., *Proc Natl Acad Sci USA* (1978) 75:4194-4198, Kim, S., et al., *Biochim Biophys Acta* (1983) 728:339:348, and Mayer, et al., *Biochim Biophys Acta* (1986) 858:161-168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol and the like. Synthetic phospholipids that may also be used, include, but are not limited to: dimyristoylphosphatidylcholine, dioleoylphosphatidylcholine, dipalmitoylphosphatidylcholine and distearoylphosphatidylcholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2,3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L., et al., *Nature* (1980) 288:602-604.

The compounds of the present invention may be used to stimulate growth of bone-forming cells or their precursors, or to induce differentiation of bone-forming cell precursors, either in vitro or ex vivo. The compounds described herein may also modify a target tissue or organ environment, so as to attract bone-forming cells to an environment in need of such cells. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan, *J. Orthop. Res.* (1991) 9:641-50). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or reinfused) into a vertebrate subject in need thereof. For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

The dosage required for the NO-bisphosphonate, whether alone or in combination with an additional agent that promotes bone (for example, in osteoporosis where an increase in bone formation is desired) is manifested as a statistically significant difference in bone mass between treatment and control groups. This difference in bone mass may be seen, for example, as a 5-20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

The dosage of the NO-bisphosphonate, whether alone or in combination with the secondary agent that promotes bone, will vary according to the extent and severity of the need for treatment, the activity of the administered compound, the general health of the subject, and other considerations well known to the skilled artisan. Generally, they can be administered to a typical human on a daily basis as an oral dose of about 0.1 mg/kg-1000 mg/kg, and more preferably from about 1 mg/kg to about 200 mg/kg. The parenteral dose will appropriately be 20-100% of the oral dose. While oral administration may be preferable in most instances where the condition is a bone deficit (for reasons of ease, patient acceptability, and the like), alternative methods of administration may be appropriate for selected compounds and selected defects or diseases. The compound levels can be monitored by any suitable methods known in the art (See, e.g., Bouley et al., *Ther. Drug. Monit.*, 23(1): 56-60 (2001); and Langmann et al., *J. Chromatogr. B. Biomed. Sci. Appl.*, 735(1):41-50 (1999)).

G. EXAMPLES

The following examples are intended to illustrate but not to limit the invention.

Example 1

High Throughput Screening

In this screen, the standard positive control was the compound 59-0008 (also denoted "OS8"), which is of the formula:

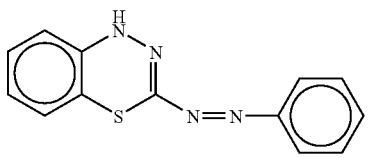

"OS8"

In more detail, the 2T3-BMP-2-LUC cells, a stably transformed osteoblast cell line described in Ghosh-Choudhury et al. *Endocrinology* (1996) 137:331-39, referenced above, was employed. The cells were cultured using α-MEM, 10% FCS with 1% penicillin/streptomycin and 1% glutamine ("plating medium"), and were split 1:5 once per week. For the assay, the cells were resuspended in a plating medium containing 4% FCS, plated in microtiter plates at a concentration of $5 \times 10^3$ cells (in 50 µl)/well, and incubated for 24 hours at 37° C. in 5% $CO_2$. To initiate the assay, 50 µl of the test compound or the control in DMSO was added at 2× concentration to each well, so that the final volume was 100 µl. The final serum concentration was 2% FCS, and the final DMSO concentration was 1%. Compound 59-0008 (10 µM) was used as a positive control.

The treated cells were incubated for 24 hours at 37° C. and 5% $CO_2$. The medium was then removed, and the cells were rinsed three times with PBS. After removal of excess PBS, 25 µl of 1× cell culture lysing reagent (Promega #E153A) was added to each well and incubated for at least ten minutes. Optionally, the plates/samples could be frozen at this point. To each well was added 50 µl of luciferase substrate (Promega #E152A; 10 ml Promega luciferase assay buffer per 7 mg Promega luciferase assay substrate). Luminescence was measured on an automated 96-well luminometer, and was expressed as either picograms of luciferase activity per well or as picograms of luciferase activity per microgram of protein.

Example 2

In Vitro Bone Formation

Selected compounds and appropriate controls were assayed in vitro (ex vivo) for bone formation activity (described above in "Techniques for Neonatal Mouse Calvaria Assay (in vitro)). Histomorphometrical assessments of ex vivo calvaria were carried out using an OsteoMetrics bone morphometry measurement program, according to the manufacturer's instructions. Measurements were determined using either a 10- or 20-fold objective with a standard point counting eyepiece graticule.

New bone formation was determined (using a 20× objective) by measuring the new bone area formed in one field in 3 representative sections of each bone (4 bones per group). Each measurement was carried out ½ field distance from the end of the suture. Both total bone and old bone area were measured. Data were expressed as new bone width in mm.

Osteoblast numbers are determined by point counting. The number of osteoblast cells lining the bone surface on both sides of the bone are counted in one field using a 20× objective. Data are expressed as osteoblast numbers/mm of bone surface.

Alkaline phosphatase activity is measured in the incubation media as detailed described above in "Techniques for Neonatal Mouse Calvaria Assay (in vitro)).

An example of the concept of a nitric oxide releasing bisphosphonate conjugate is seen where O-Nitroso analogue is linked to alendronate (4-animo-1-hydroxybutylidene)bisphosphonate (FIG. 1) to make [4-(4'-nitrooxymethyl)benzoylamino-1-hydroxybutylidene]-bis-phosphonate (NOX-alendronate) (FIG. 2)

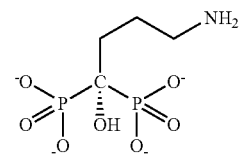

Alendronate

Figure 1

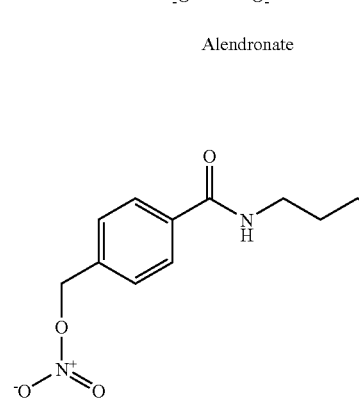

NOX-alendronate

Figure 2

TABLE 1

Stimulation New Bone Formation on Neonatal Murine Calvariae with NOX-Alendronate

| uM NOX-Alendronate | New Bone Area ($mm^2 \times 10^{-3}$) | Cell Number/0.3 mm bone |
|---|---|---|
| 0 | 3.5 ± 0.2 | 95 ± 7 |
| 0.1 | 3.6 ± 0.6 | 104 ± 8 |
| 1 | 4.2 ± 0.4 | 115 ± 5 |
| 10 | 6.7 ± 0.7* | 132 ± 5* |
| 100 | 5.4 ± 0.3* | 124 ± 2* |

TABLE 2

Stimulation New Bone Formation on Neonatal Murine Calvariae with Alendronate

| uM Alendronte | New Bone Area ($mm^2 \times 10^{-3}$) | Cell Number/0.3 mm bone |
|---|---|---|
| 0 | 3.1 ± 0.3 | 96 ± 5 |
| 0.1 | 2.9 ± 0.1 | 98 ± 6 |
| 1.0 | 3.2 ± 0.5 | 103 ± 4 |
| 10 | 2.7 ± 0.2 | 101 ± 5 |
| 100 | 3.1 ± 0.3 | 97 ± 3 |

TABLE 3

Alkaline phosphatase activity in neonatal murine calvarial incubation media from bones treated with either NOX-Alendronate or Alendronate

| uM | Alkaline Phosphatase OD NOX-Alendronate | Alkaline Phosphatase OD Alendronate |
|---|---|---|
| 0 | 0.024 ± 0.006 | 0.027 ± 0.006 |
| 0.1 | 0.029 ± 0.007 | 0.030 ± 0.009 |
| 1 | 0.023 ± 0.001 | 0.031 ± 0.010 |
| 10 | 0.053 ± 0.007* | 0.034 ± 0.001 |
| 100 | 0.072 ± 0.003* | 0.038 ± 0.003 |

The numbers represent the mean±standard error (n=5). *$p<0.05$, t-test or one-way analysis of variance (ANOVA) followed by Dunnett's test.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

Citation of the above documents is not intended as an admission that any of the foregoing is pertinent prior art, nor does it constitute any admission as to the contents or date of these documents.

I claim:

1. A method to enhance bone formation in a vertebrate animal comprising administering to the vertebrate animal in need of such enhancement a therapeutically-effective amount of a covalent conjugate consisting of a bisphosphonate and a nitric oxide (NO) releasing compound, (an NO-bisphosphonate).

2. The method of claim 1 wherein the bisphosphonate is alendronate, pamidronate, clodronate, zoledronate, risedronate, etidronate, ibandronate, tiludronate, neridronate, olpadronate, incadronate or YH529.

3. The method of claim 1 wherein the vertebrate animal is a mammal.

4. The method of claim 3 wherein the mammal is a human.

5. The method of claim 1 wherein the NO-bisphosphonate is administered with a pharmaceutically acceptable carrier or excipient.

6. The method of claim 1 wherein the animal has/is suffering from osteoporosis, a bone fracture or deficiency, primary or secondary hyperparathyroidism, periodontal disease or defect, metastatic bone disease, bone graft, bone segmental defect, osteolytic bone disease, post-plastic surgery, post-prosthetic joint surgery degenerative joint condition, post-dental implantation, or cartilage disorder or injury.

7. The method of claim 1 further comprising administering to the animal an additional agent that enhances bone growth or decreases bone resorption.

8. The method of claim 7 wherein the agent is a bone morphogenic protein, growth hormone, estrogen, statin, bisphosphonate, osteogenic factor, anti-resorptive agent, cartilage-derived morphogenic protein, differentiating factor, bone-growth stimulating compound, NF-κB inhibitor, proteasomal inhibitor, proteasomal production inhibitor, or steroid.

9. The method of claim 7 wherein the conjugate and additional agent are administered simultaneously or sequentially.

10. The method of claim 7 wherein the conjugate and additional agent are formulated in a single pharmaceutical formulation or each is formulated in a separate pharmaceutical formulation.

* * * * *